(12) United States Patent
Ding et al.

(10) Patent No.: US 12,037,648 B2
(45) Date of Patent: Jul. 16, 2024

(54) KITS AND METHODS FOR PEDIGREE DIVISION AND PATERNITY TESTING OF DOMESTIC PIGS

(71) Applicant: ANHUI AGRICULTURAL UNIVERSITY, Anhui (CN)

(72) Inventors: Yueyun Ding, Hefei (CN); Xiaoling Ding, Hefei (CN); Zongjun Yin, Hefei (CN); Xudong Wu, Hefei (CN); Xiaodong Zhang, Hefei (CN); Xianrui Zheng, Hefei (CN); Zijing Ling, Hefei (CN); Qiong Chen, Hefei (CN); Yinhui Hou, Hefei (CN); Chengcheng Kong, Hefei (CN)

(73) Assignee: ANHUI AGRICULTURAL UNIVERSITY, Hefei (CN)

( * ) Notice: Subject to any disclaimer, the term of this patent is extended or adjusted under 35 U.S.C. 154(b) by 149 days.

(21) Appl. No.: 17/811,594

(22) Filed: Jul. 11, 2022

(65) Prior Publication Data

US 2023/0042006 A1  Feb. 9, 2023

(30) Foreign Application Priority Data

Jul. 12, 2021  (CN) .................. 202110782383.2

(51) Int. Cl.
  *C12Q 1/6888*  (2018.01)
  *C12Q 1/6858*  (2018.01)

(52) U.S. Cl.
  CPC .......... *C12Q 1/6888* (2013.01); *C12Q 1/6858* (2013.01); *C12Q 2600/124* (2013.01); *C12Q 2600/156* (2013.01)

(58) Field of Classification Search
  CPC .................................................. C12Q 1/6888
  See application file for complete search history.

(56) References Cited

U.S. PATENT DOCUMENTS

2010/0209911 A1* 8/2010 Ju ........................ C12Q 1/6888
536/23.1

FOREIGN PATENT DOCUMENTS

| CN | 102154280 | A |   | 8/2011  |           |
|----|-----------|---|---|---------|-----------|
| CN | 105039518 | A | * | 11/2015 | C12Q 1/6858 |
| CN | 105039518 | A |   | 11/2015 |           |
| CN | 106244717 | A |   | 12/2016 |           |
| CN | 111363830 | A |   | 7/2020  |           |
| CN | 112126693 | A |   | 12/2020 |           |
| CN | 108728520 | B |   | 9/2021  |           |
| JP | 2008092904 | A |  | 4/2008  |           |
| KR | 20090011636 | A | | 2/2009  |           |
| RU | 2744733   | C1 |  | 3/2021  |           |

OTHER PUBLICATIONS

Li, Qinggang et al., Genetic Diversity Analysis Based on Microsatellite Markers in Five Anhui Local and Five Introduced Pig Breeds, Swine Production, 3: 67-72, 2018.
Ruan, Hongyue et al., An Application Research of Fourteen Microsatellite DNA Markers in Identification of Individuals and Traceability in Pig, Journal of Agricultural Biotechnology, 18(6): 1129-1133, 2010.
Radoslav Zidek et al., Genetic admixture in pig population observed by microsatellite makers, Achieve Tierzucht, 54: 51-60, 2011.
Polona Margeta et al., 12-plex highly polymorphic microsatellite marker set for parentage analysis in Banjia spotted pigs, journal of central European agriculture 20(1): 50-54, 2019.
Vania costa et al., Microsatellite makers for identification and parentage analysis in the European wild boar (*Susscrofa*), BMC research notes, 5(479): 1-6, 2012.
Notification to Grant Patent Right for Invention in Chinese Application No. 20211078238.3 mailed on Jun. 28, 2023, 6 pages.

* cited by examiner

*Primary Examiner* — Aaron A Priest
*Assistant Examiner* — Tian Yu
(74) *Attorney, Agent, or Firm* — METIS IP LLC (57) ABSTRACT

The present disclosure belongs to the field of livestock molecular biotechnology, and provides kits and methods for pedigree division and paternity testing of domestic pigs. The kits and methods specifically select 14 SSR loci of domestic pigs, especially Anqing six-end-white pigs, and synthesize primers for corresponding loci. Through capillary electrophoresis detection of the ear tissue DNA of 98 Anqing six-end-white pigs, the count of effective alleles, heterozygosity, polymorphism information content, and genetic distance, and exclusion probability at each locus are calculated, the pedigree division of domestic pigs, especially Anqing six-end-white pigs, and paternity testing are conducted. The cumulative exclusion probability of 14 microsatellite loci is 99%. The 14 microsatellite loci selected are polymorphic in Anqing six-end-white pig population, which can be used as effective genetic markers in the production practice of domestic pigs, especially in the pedigree division and paternity testing of Anqing six-end-white pig population.

8 Claims, 3 Drawing Sheets
Specification includes a Sequence Listing.

SEQUENCE LISTING

```
Sequence total quantity: 28
SEQ ID NO: 1                moltype = DNA  length = 24
FEATURE                     Location/Qualifiers
source                      1..24
                            mol_type = other DNA
                            organism = synthetic construct
SEQUENCE: 1
tgttctctgt ttctcctctg tttg                                            24

SEQ ID NO: 2                moltype = DNA  length = 27
FEATURE                     Location/Qualifiers
source                      1..27
                            mol_type = other DNA
                            organism = synthetic construct
SEQUENCE: 2
gttaaagtgg aaagagtcaa tggctat                                         27

SEQ ID NO: 3                moltype = DNA  length = 22
FEATURE                     Location/Qualifiers
source                      1..22
                            mol_type = other DNA
                            organism = synthetic construct
SEQUENCE: 3
agaaattagt gcctcaaatt gg                                              22

SEQ ID NO: 4                moltype = DNA  length = 22
FEATURE                     Location/Qualifiers
source                      1..22
                            mol_type = other DNA
                            organism = synthetic construct
SEQUENCE: 4
aaaccattaa gtccctagca aa                                              22

SEQ ID NO: 5                moltype = DNA  length = 17
FEATURE                     Location/Qualifiers
source                      1..17
                            mol_type = other DNA
                            organism = synthetic construct
SEQUENCE: 5
tcagaacagt gcgccgt                                                    17

SEQ ID NO: 6                moltype = DNA  length = 21
FEATURE                     Location/Qualifiers
source                      1..21
                            mol_type = other DNA
                            organism = synthetic construct
SEQUENCE: 6
gtttgaaaat ggggtgtttc c                                               21

SEQ ID NO: 7                moltype = DNA  length = 27
FEATURE                     Location/Qualifiers
source                      1..27
                            mol_type = other DNA
                            organism = synthetic construct
SEQUENCE: 7
gatccattta taattttagc acaaagt                                         27

SEQ ID NO: 8                moltype = DNA  length = 24
FEATURE                     Location/Qualifiers
source                      1..24
                            mol_type = other DNA
                            organism = synthetic construct
SEQUENCE: 8
gcatggtgtg atgctatgtc aagc                                            24

SEQ ID NO: 9                moltype = DNA  length = 19
FEATURE                     Location/Qualifiers
source                      1..19
                            mol_type = other DNA
                            organism = synthetic construct
SEQUENCE: 9
tctgttgttt cccaccagc                                                  19

SEQ ID NO: 10               moltype = DNA  length = 22
FEATURE                     Location/Qualifiers
source                      1..22
                            mol_type = other DNA
                            organism = synthetic construct
```

```
SEQUENCE: 10
tgtgcacctg acacatagac tc                                               22

SEQ ID NO: 11          moltype = DNA   length = 23
FEATURE                Location/Qualifiers
source                 1..23
                       mol_type = other DNA
                       organism = synthetic construct
SEQUENCE: 11
ttgtctttt atttttgcttt tgg                                              23

SEQ ID NO: 12          moltype = DNA   length = 22
FEATURE                Location/Qualifiers
source                 1..22
                       mol_type = other DNA
                       organism = synthetic construct
SEQUENCE: 12
caaaaaaggc aaagattga ca                                                22

SEQ ID NO: 13          moltype = DNA   length = 23
FEATURE                Location/Qualifiers
source                 1..23
                       mol_type = other DNA
                       organism = synthetic construct
SEQUENCE: 13
gaatgcaaag agttcagtgt agg                                              23

SEQ ID NO: 14          moltype = DNA   length = 22
FEATURE                Location/Qualifiers
source                 1..22
                       mol_type = other DNA
                       organism = synthetic construct
SEQUENCE: 14
gtctccctca cacttaccgc ag                                               22

SEQ ID NO: 15          moltype = DNA   length = 22
FEATURE                Location/Qualifiers
source                 1..22
                       mol_type = other DNA
                       organism = synthetic construct
SEQUENCE: 15
gctaatgcca gagaaatgca ga                                               22

SEQ ID NO: 16          moltype = DNA   length = 22
FEATURE                Location/Qualifiers
source                 1..22
                       mol_type = other DNA
                       organism = synthetic construct
SEQUENCE: 16
caggtggaaa gaatggaatg aa                                               22

SEQ ID NO: 17          moltype = DNA   length = 23
FEATURE                Location/Qualifiers
source                 1..23
                       mol_type = other DNA
                       organism = synthetic construct
SEQUENCE: 17
gaactcctgg gtcttatttt cta                                              23

SEQ ID NO: 18          moltype = DNA   length = 29
FEATURE                Location/Qualifiers
source                 1..29
                       mol_type = other DNA
                       organism = synthetic construct
SEQUENCE: 18
gtcaaaaatc ttttatctc caacagtat                                         29

SEQ ID NO: 19          moltype = DNA   length = 24
FEATURE                Location/Qualifiers
source                 1..24
                       mol_type = other DNA
                       organism = synthetic construct
```

-continued

```
SEQUENCE: 19
ccaagactgc cttgtaggtg aata                                              24

SEQ ID NO: 20           moltype = DNA   length = 24
FEATURE                 Location/Qualifiers
source                  1..24
                        mol_type = other DNA
                        organism = synthetic construct
SEQUENCE: 20
gctatcaagt attgtaccat tagg                                              24

SEQ ID NO: 21           moltype = DNA   length = 26
FEATURE                 Location/Qualifiers
source                  1..26
                        mol_type = other DNA
                        organism = synthetic construct
SEQUENCE: 21
tctggctcct acactccttc ttgatc                                            26

SEQ ID NO: 22           moltype = DNA   length = 26
FEATURE                 Location/Qualifiers
source                  1..26
                        mol_type = other DNA
                        organism = synthetic construct
SEQUENCE: 22
gtttgggtgg gtgctgaaaa atagga                                            26

SEQ ID NO: 23           moltype = DNA   length = 19
FEATURE                 Location/Qualifiers
source                  1..19
                        mol_type = other DNA
                        organism = synthetic construct
SEQUENCE: 23
ctttgggtgg agtgtgtgc                                                    19

SEQ ID NO: 24           moltype = DNA   length = 18
FEATURE                 Location/Qualifiers
source                  1..18
                        mol_type = other DNA
                        organism = synthetic construct
SEQUENCE: 24
atccaaatgc tgcaagcg                                                     18

SEQ ID NO: 25           moltype = DNA   length = 20
FEATURE                 Location/Qualifiers
source                  1..20
                        mol_type = other DNA
                        organism = synthetic construct
SEQUENCE: 25
aaccttccct tcccaatcac                                                   20

SEQ ID NO: 26           moltype = DNA   length = 20
FEATURE                 Location/Qualifiers
source                  1..20
                        mol_type = other DNA
                        organism = synthetic construct
SEQUENCE: 26
cacagactgc tttttactcc                                                   20

SEQ ID NO: 27           moltype = DNA   length = 20
FEATURE                 Location/Qualifiers
source                  1..20
                        mol_type = other DNA
                        organism = synthetic construct
SEQUENCE: 27
caagtgccca tcaacacttg                                                   20

SEQ ID NO: 28           moltype = DNA   length = 22
FEATURE                 Location/Qualifiers
source                  1..22
                        mol_type = other DNA
                        organism = synthetic construct
SEQUENCE: 28
tcatctctgg gtccatctta cg                                                22
```

KITS AND METHODS FOR PEDIGREE DIVISION AND PATERNITY TESTING OF DOMESTIC PIGS

CROSS-REFERENCE TO RELATED APPLICATIONS

This application claims priority of Chinese Patent Application No. 202110782383.2, filed on Jul. 12, 2021, the entire contents of which are hereby incorporated by reference.

SEQUENCE LISTING

The instant application contains a Sequence Listing which has been submitted electronically in XML format and is hereby incorporated by reference in its entirety. The XML copy, created on Aug. 10, 2022, is named "Sequence Listing-61801-0001US00" and is 25,802 bytes in size.

TECHNICAL FIELD

The present disclosure relates to the field of livestock molecular biotechnology, and more particular to kits and methods for pedigree division and paternity testing of domestic pigs.

BACKGROUND

The protection of pig breeding resources depends on local breeding farms. In the production process, there are many introductions, unclear records of pedigree and production information, resulting in unclear genetic relationships of pigs in stock and increased inbreeding risk, which directly leads to the decline of the number of high-quality breeding pig families, the reduction of variety purity and genetic diversity, and seriously affects the preservation of high-quality germplasm resources of breeding pig and industrial development. Therefore, accurate genetic relationship is of great significance for formulating pig breeding plans, avoiding inbreeding, seed retention selection and speeding up the breeding process.

Simple sequence repeats (SSR) are a kind of microsatellite loci with 2-6 bp size that repeats multiple times, which widely exist in the genome of organisms, have the characteristics of strong specificity, high genome coverage, and rich genetic markers, in line with the co-dominance of Mendelian genetic law.

In view of the current gap in the protection of local pigs, especially Anqing six-end-white pig germplasm resources, it is desirable to develop a method for pedigree division and paternity testing of Anqing six-end-white pigs by SSR molecular marker technology to analyze the genetic diversity of Anqing six-end-white pig population, help the resources protection and industrial development of Anqing six-end-white pig germplasm. The pedigree division and paternity testing of domestic pigs, especially Anqing six-end-white pigs, has very important experimental and production significance for further developing Anqing six-end-white pig breeding, tapping its potential and protecting variety resources.

SUMMARY

The purpose of the present disclosure is to analyze the genetic diversity of Anqing six-end-white pig population by using SSR molecular marker technology in view of the current gap in the protection of domestic pigs, especially Anqing six-end-white pig germplasm resources, and explore a method of pedigree division and paternity testing of Anqing six-end-white pig based on SSR markers, so as to contribute to the protection and industrial development of Anqing six-end-white pig germplasm resources.

The present disclosure provides a kit for pedigree division and paternity testing of domestic pigs. The kit includes 14 SSR loci. The SSR loci includes S0155 microsatellite loci on chromosome 1, SW240 microsatellite loci on chromosome 2, SW72 microsatellite loci on chromosome 3, and S0227 microsatellite loci on chromosome 4 respectively; SW963 microsatellite loci on chromosome 5; SW122 microsatellite loci on chromosome 6; S0101 microsatellite loci on chromosome 7; S0225 microsatellite loci on chromosome 8; S0386 microsatellite loci on chromosome 11; S0090 microsatellite loci on chromosome 12; S0355 microsatellite loci on chromosome 15; S0026 microsatellite loci on chromosome 16; SW24 microsatellite loci on chromosome 17; and SW2156 microsatellite loci on sex chromosome.

Further, the primers required for PCR amplification of the 14 SSR loci are as follows: the forward primer sequence of S0155 microsatellite loci is shown in SEQ ID No. 1, and the reverse primer sequence is shown in SEQ ID No. 2; the forward primer sequence of SW240 microsatellite loci is shown in SEQ ID No. 3, and the reverse primer sequence is shown in SEQ ID No. 4; the forward primer sequence of SW72 microsatellite loci is shown in SEQ ID No. 5, and the reverse primer sequence is shown in SEQ ID No. 6; the forward primer sequence of SW963 microsatellite loci shown in SEQ ID No. 7 and reverse primer sequence is shown in SEQ ID No. 8; the forward primer sequence of SW963 microsatellite loci is shown in SEQ ID No. 9, and reverse primer sequence is shown in SEQ ID No. 10; the forward primer sequence of SW122 microsatellite loci is shown in SEQ ID No. 11, and the reverse primer sequence is shown in SEQ ID No. 12; the forward primer sequence of S0101 microsatellite loci is shown in SEQ ID No. 13, and reverse primer sequence is shown in SEQ ID No. 14; the forward primer sequence of S0101 microsatellite loci is shown in SEQ ID No. 15, reverse primer sequence is shown in SEQ ID No. 16; the forward primer sequence of S0101 microsatellite loci is shown in SEQ ID No. 17, reverse primer sequence is shown in SEQ ID No. 18; the forward primer sequence of S0101 microsatellite loci is shown in SEQ ID No. 19, reverse primer sequence is shown in SEQ ID No. 20; the forward primer sequence of S0101 microsatellite loci is shown in SEQ ID No. 21, and reverse primer sequence is shown in SEQ ID No. 22; the forward primer sequence of 50026 microsatellite loci is shown in SEQ ID No. 23, and reverse primer sequence is shown in SEQ ID No. 24; the forward primer sequence of SW24 microsatellite loci is shown in SEQ ID No. 25, and the reverse primer sequence is shown in SEQ ID No. 26; the forward primer sequence of SW2156 microsatellite loci is shown in SEQ ID No. 27, and reverse primer sequence is shown in SEQ ID No. 28.

Further, loci S0155, SW963, and S0386 are fluorescent-labeled as 5'-FAM, loci SW240, SW72, SW122, SW24, and 50026 are fluorescent-labeled as 5'-HEX, and loci S0227, S0101, S0090, and S0355 are fluorescent-labeled as 5' TAMRA. The PCR annealing temperature of loci S0155, SW240, SW72, 50227, SW963, S0101, S0225, S0386, S0090, S0355 and SW24 are 55° C., the PCR annealing temperature of locus SW122 is 58.5° C. and the annealing temperature of locus SW2156 is 60° C.

Further, the kit is 25 μL reaction system, including 1 μL upstream primer, 1 μL downstream primer, 1 μL mix dNTR, 2.5 μL includes MgCl$_2$ Taq Buffer, 0.5 μL Taq enzyme, 19 μL ddH$_2$O.

Further, the 14 SSR loci may be applied to Anqing six-end-white pigs.

The present disclosure also provides a method for pedigree division and paternity testing of domestic pigs, which includes synthesizing primers required for PCR amplification of SSR loci of the domestic pigs, the primers are the primers described above.

Further, the method further includes: collecting samples from the domestic pigs; extracting DNA from the samples by using a rapid genomic DNA extraction kit; performing PCR amplification with the primers to obtain PCR products; detecting PCR products by capillary electrophoresis to obtain a detection result; and performing data processing and results analysis for the detection result.

Further, the performing data processing and results analysis for the detection result includes: using Popgene3.2 software to perform the analysis of a count of alleles, a count of effective alleles, an observed homozygosity, an expected homozygosity, an observed heterozygosity, an expected heterozygosity, a Shannon index and a hard Weinberg equilibrium index of each microsatellite locus; using PIC_Cale0.6 software to calculate a polymorphic information content; using the DiploidDate program to calculate Nei's genetic distance between individuals, and obtaining the phylogenetic cluster diagram constructed by the Unweighted Pair-group Method with Arithmetic Mean (UPGMA).

Further, the domestic pig is Anqing six-end-white pig and the samples are collected from ears of the domestic pigs.

Further, the performing PCR amplification with the primers to obtain PCR products: performing pre denaturation at 95° C. for 3 minutes; denaturation at 94° C. for 30 seconds, annealing at 60° C. for 30 seconds, extension at 72° C. for 30 seconds, 10 cycles; denaturation at 94° C. for 30 seconds, annealing at 55° C. for 30 seconds, extension at 72° C. for 30 seconds, 35 cycles; repair and extension at 72° C. for 8 minutes.

The present disclosure has the following advantages:

1. In view of the gap in pedigree division and paternity testing of Anqing six-end-white pigs, 14 SSR loci are specifically selected and PCR is carried out through synthetic primers. The pedigree division of SSR marker information is consistent with the production records. Therefore, the family conditions of Anqing six-end-white pigs can be quickly obtained through molecular identification. The cumulative exclusion probability of NE-1P, NE-2P, and NE-PP of the 14 microsatellite loci selected are more than 99%, which meet the requirements of paternity testing among different individuals in production practice.

2. The selected 14 SSR loci belong to different chromosomes, and the possibility of linkage between them is small. The 14 microsatellite loci have specific allele distribution in Anqing six-end-white pig population.

3. The position for DNA collection in this method is pig ear, which can decrease damage for pigs to obtain pig DNA, and is conducive to production practice. According to this method, by PCR amplification based on 14 SSR loci, the breeding accuracy of domestic pigs, especially Anqing six-end-white pigs, can be improved, the breeding process can be speeded up, thereby having good application prospects and economic benefits.

DETAILED DESCRIPTION

The terminology used herein is for the purposes of describing particular examples and embodiments only and is not intended to be limiting. As used herein, the singular forms "a," "an," and "the" may be intended to include the plural forms as well, unless the context clearly indicates otherwise. It will be further understood that the terms "include" and/or "comprise," when used in this disclosure, specify the presence of integers, behaviors, stated features, steps, elements, and/or operations, but do not exclude the presence or addition of one or more other integers, behaviors, features, steps, elements, operations, and/or groups thereof.

According to one aspect of the present disclosure, a kit for pedigree division and paternity testing of domestic pigs is provided. The kit includes a plurality of SSR loci. The SSR loci include a SW72 microsatellite locus on chromosome 3, a SW963 microsatellite locus on chromosome 5, a S0101 microsatellite locus on chromosome 7, a S0386 microsatellite locus on chromosome 11, a S0090 microsatellite locus on chromosome 12, a SW24 microsatellite locus on chromosome 17, and a SW2156 microsatellite locus on sex chromosome. The SSR loci further include a S0155 microsatellite locus on chromosome 1, a SW240 microsatellite locus on chromosome 2, a S0227 microsatellite locus on chromosome 4, a SW122 microsatellite locus on chromosome 6, a S0225 microsatellite locus on chromosome 8, a S0355 microsatellite locus on chromosome 15, and a S0026 microsatellite locus on chromosome 16.

In some embodiments, primers required for PCR amplification of the SSR loci includes: a forward primer sequence of the SW72 microsatellite locus shown in SEQ ID No. 5 and a reverse primer sequence of the SW72 microsatellite locus shown in SEQ ID No. 6; a forward primer sequence of the SW963 microsatellite locus shown in SEQ ID No. 9 and a reverse primer sequence of the SW963 microsatellite locus shown in SEQ ID No. 10; a forward primer sequence of the S0101 microsatellite locus shown in SEQ ID No. 13 and a reverse primer sequence of the S0101 microsatellite locus shown in SEQ ID No. 14; a forward primer sequence of the S0386 microsatellite locus shown in SEQ ID No. 17 and a reverse primer sequence of the S0386 microsatellite locus shown in SEQ ID No. 18; a forward primer sequence of the S0090 microsatellite locus shown in SEQ ID No. 19 and a reverse primer sequence of the S0090 microsatellite locus shown in SEQ ID No. 20; a forward primer sequence of the SW24 microsatellite locus shown in SEQ ID No. 25 and a reverse primer sequence of the SW24 microsatellite locus shown in SEQ ID No. 26; and a forward primer sequence of the SW2156 microsatellite locus shown in SEQ ID No. 27 and a reverse primer sequence of the SW2156 microsatellite locus shown in SEQ ID No. 28.

In some embodiments, the primers further include a forward primer sequence of the S0155 microsatellite locus shown in SEQ ID No. 1 and a reverse primer sequence of the S0155 microsatellite locus shown in SEQ ID No. 2; a forward primer sequence of the SW240 microsatellite locus shown in SEQ ID No. 3 and a reverse primer sequence of the SW240 microsatellite locus shown in SEQ ID No. 4; a forward primer sequence of the SW227 microsatellite locus shown in SEQ ID No. 7 and a reverse primer sequence of the SW227 microsatellite locus shown in SEQ ID No. 8; a forward primer sequence of the SW122 microsatellite locus shown in SEQ ID No. 11 and a reverse primer sequence of the SW122 microsatellite locus shown in SEQ ID No. 12; a forward primer sequence of the S0225 microsatellite locus shown in SEQ ID No. 15 and a reverse primer sequence of the S0225 microsatellite locus shown in SEQ ID No. 16; a forward primer sequence of the S0355 microsatellite locus shown in SEQ ID No. 21 and a reverse primer sequence of the S0355 microsatellite locus shown in SEQ ID No. 22; and a forward primer sequence of the S0026 microsatellite locus shown in SEQ ID No. 23 and a reverse primer sequence of the S0026 microsatellite locus shown in SEQ ID No. 24.

In some embodiments, the S0155 microsatellite locus, SW963 microsatellite locus, and S0386 microsatellite locus are fluorescent-labeled as 5'-FAM, the SW240 microsatellite locus, the SW72 microsatellite locus, the SW122 microsatellite locus, the SW24 microsatellite locus, and the S0026 microsatellite locus are fluorescent-labeled as 5'-HEX, and the S0227 microsatellite locus, the S0101 microsatellite locus, the S0090 microsatellite locus, and the S0355 microsatellite locus are fluorescent-labeled as 5'TAMRA. A PCR annealing temperature of the S0155 microsatellite locus, the SW240 microsatellite locus, the SW72 microsatellite locus, the S0227 microsatellite locus, the SW963 microsatellite locus, the S0101 microsatellite locus, the S0225 microsatellite locus, the S0386 microsatellite locus, the S0090 microsatellite locus, the S0355 microsatellite locus and the SW24 microsatellite locus are 55° C., the PCR annealing temperature of the SW122 microsatellite locus is 58.5° C. and the annealing temperature of the SW2156 microsatellite locus is 60° C.

The kit is a 25 μL reaction system, comprising a 1 μL upstream primer, a 1 μL downstream primer, a 1 μL mix dNTR, a 2.5 μL MgCl₂ Taq Buffer, a 0.5 μL Taq enzyme, and 19 μL ddH₂O.

The domestic pigs are Anqing six-end-white pigs.

According to other aspect of the present disclosure, a method for pedigree division and paternity testing of domestic pigs is provided. The method includes:

(1) collecting samples from the domestic pigs;
(2) extracting DNA from the samples by using the rapid genomic DNA extraction kit of Beijing Adlai biotechnology company;
(3) synthesizing primers required for PCR amplification of the SSR loci, the primers including the primers of claim 3;
(4) performing PCR amplification with the primers to obtain PCR products;
(5) detecting PCR products by capillary electrophoresis to obtain a detection result; and
(6) data processing and results analysis for the detection result.

In some embodiments, the step of (6) includes using Popgene3.2 software to perform an analysis of a count of alleles, a count of effective alleles, an observed homozygosity, an expected homozygosity, an observed heterozygosity, an expected heterozygosity, a Shannon index and a hard Weinberg equilibrium index of each microsatellite locus; using PIC_Cale0.6 software to calculate a polymorphic information content; using the DiploidDate program to calculate a Nei's genetic distance between individuals; and obtaining a phylogenetic cluster diagram constructed by the unweighted pair-group method with arithmetic mean (UPGMA).

The domestic pigs are Anqing six-end-white pigs and the samples are collected from pig ears.

The step of (4) performing PCR amplification with the primers to obtain PCR products comprises: performing pre denaturation at 95° C. for 3 minutes; performing denaturation at 94° C. for 30 seconds, annealing at 60° C. for 30 seconds, performing extension at 72° C. for 30 seconds for 10 cycles; performing denaturation at 94° C. for 30 seconds, annealing at 55° C. for 30 seconds, performing extension at 72° C. for 30 seconds for 35 cycles; and performing repairing and extension at 72° C. for 8 minutes.

The present disclosure is described in detail below in combination with specific examples.

Example 1

1 Material Method:
1.1 Sample Collection

The present disclosure collects ear tissue samples of 98 pure Anqing six-end-white pigs, which are provided by Anhui Huating Lake Green Food Development Co., Ltd. (Chengling village, Jinxi Town, Taihu County, Anqing City, Anhui Province). The ear tissue samples are stored in a 1.5 ml centrifuge tube filled with 500 μL of 75% alcohol, which are brought back to the laboratory and stored at −20° C.

1.2 DNA Extraction

The tissue DNA of Anqing six-end-white pigs is extracted with the rapid extraction kit of tissue genomic DNA of Adlai biotechnology company (Beijing). The extracted DNA samples are checked for concentration and purity by ultraviolet spectrophotometer. The qualified DNA samples are stored at −80° C. for standby.

1.3 Microsatellite Loci Selection and Primer Design

The information of the 14 loci selected by the present disclosure is shown in Table 1. The primer sequences of the corresponding loci are synthesized according to the locus information. See Table 1 for the locus information and primer sequences.

TABLE 1

Microsatellite loci and primer information

| Microsatellite loci (SSR) | Chromosomal location | Primer sequence (5'-3') | Annealing temperature (° C.) | Fluorescent label |
|---|---|---|---|---|
| S0155 | 1 | TGTTCTCTGTTTCTCCTCTGTTTG (SEQ ID No. 1) GTTAAAGTGGAAAGAGTCAATGGCTAT (SEQ ID No. 2) | 55 | 5'-FAM |

TABLE 1-continued

Microsatellite loci and primer information

| Microsatellite loci (SSR) | Chromosomal location | Primer sequence (5'-3') | Annealing temperature (° C.) | Fluorescent label |
|---|---|---|---|---|
| SW240 | 2 | AGAAATTAGTGCCTCAAATTGG (SEQ ID No. 3) AAACCATTAAGTCCCTAGCAAA (SEQ ID No. 4) | 55 | 5'-HEX |
| SW72 | 3 | TCAGAACAGTGCGCCGT (SEQ ID No. 5) GTTTGAAAATGGGTGTTTCC (SEQ ID No. 6) | 55 | 5'-HEX |
| S0227 | 4 | GATCCATTTATAATTTTAGCACA AAGT (SEQ ID No. 7) GCATGGTGTGATGCTATGTCAAG C (SEQ ID No. 8) | 55 | 5'-TAMRA |
| SW963 | 5 | TCTGTTGTTTCCCACCAGC (SEQ ID No. 9) TGTGCACCTGACACATAGACTC (SEQ ID No. 10) | 55 | 5'-FAM |
| SW122 | 6 | TTGTCTTTTTATTTTGCTTTTGG (SEQ ID No. 11) CAAAAAAGGCAAAAGATTGACA (SEQ ID No. 12) | 58.5 | 5'-HEX |
| S0101 | 7 | GAATGCAAAGAGTTCAGTGTAG G(SEQ ID No. 13) GTCTCCCTCACACTTACCGCAG (SEQ ID No. 14) | 55 | 5'-TAMRA |
| S0225 | 8 | GCTAATGCCAGAGAAATGCAGA (SEQ ID No. 15) CAGGTGGAAAGAATGGAATGAA (SEQ ID No. 16) | 55 | 5'-FAM |
| S0386 | 11 | GAACTCCTGGGTCTTATTTTCTA (SEQ ID No. 17) GTCAAAAATCTTTTTATCTCCAA CAGTAT (SEQ ID No. 18) | 55 | 5'-FAM |
| S0090 | 12 | CCAAGACTGCCTTGTAGGTGAA TA (SEQ ID No. 19) GCTATCAAGTATTGTACCATTAG G (SEQ ID No. 20) | 55 | 5'-TAMRA |
| S0355 | 15 | TCTGGCTCCTACACTCCTTCTTG ATC (SEQ ID No. 21) GTTTGGGTGGGTGCTGAAAAAT AGGA (SEQ ID No. 22) | 55 | 5'-TAMRA |
| SW24 | 17 | CTTTGGGTGGAGTGTGTGC(SEQ ID No. 23) ATCCAAATGCTGCAAGCG (SEQ ID No. 24) | 55 | 5'HEX |
| S0026 | 16 | AACCTTCCCTTCCCAATCAC (SEQ ID No. 25) CACAGACTGCTTTTTACTCC (SEQ ID No. 26) | 58.5 | 5'HEX |
| SW2156 | X.Y | CAAGTGCCCATCAACACTTG (SEQ ID No. 27) TCATCTCTGGGTCCATCTTACG (SEQ ID No. 28) | 60 | 5'-FAM |

1.4 PCR Amplification System and Reaction Conditions

Figure 1:
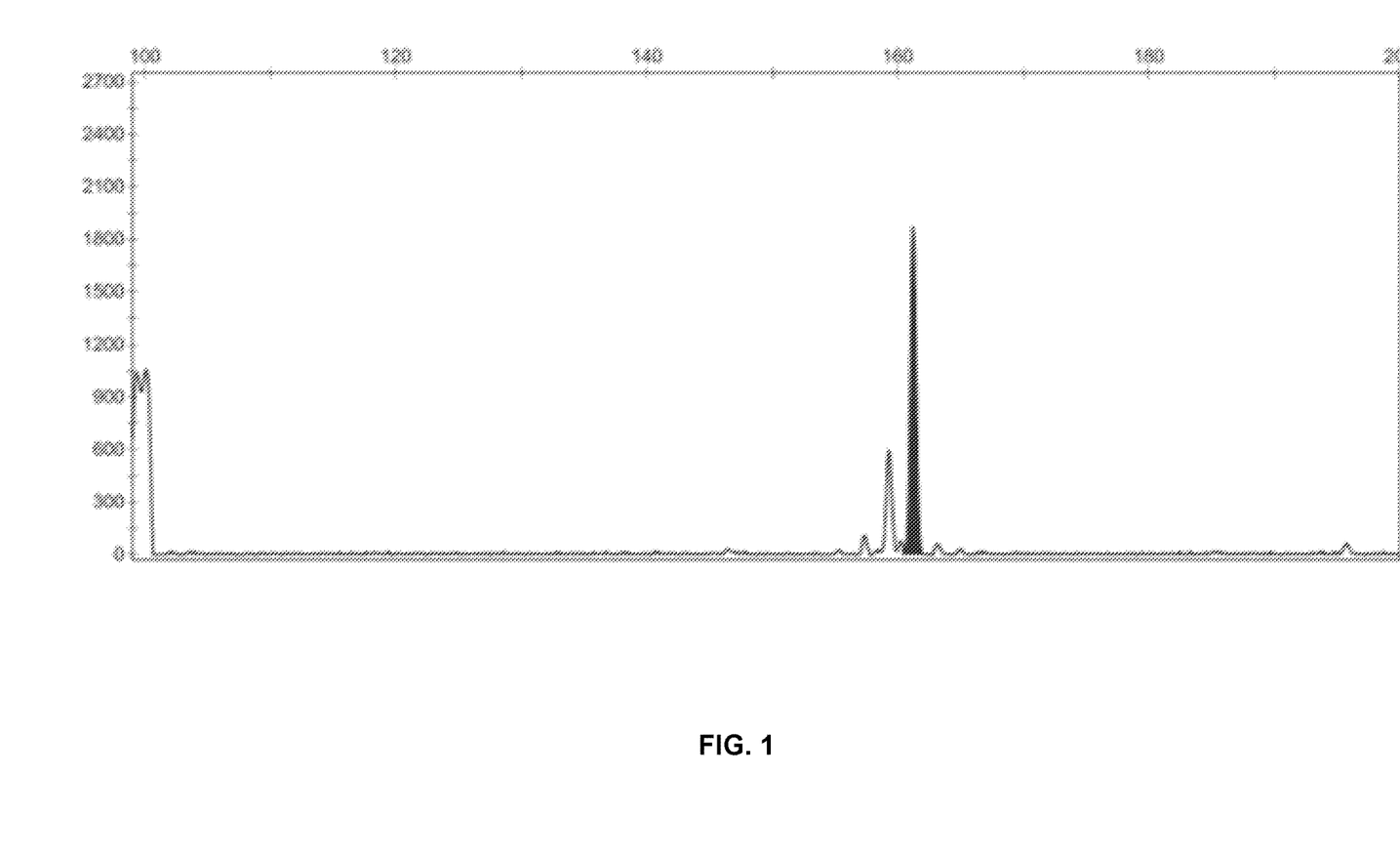
FIG. 1 shows the electrophoresis results of sample 65 at S0155 locus under fluorescent labeling 5'-FAM.
Figure 2:
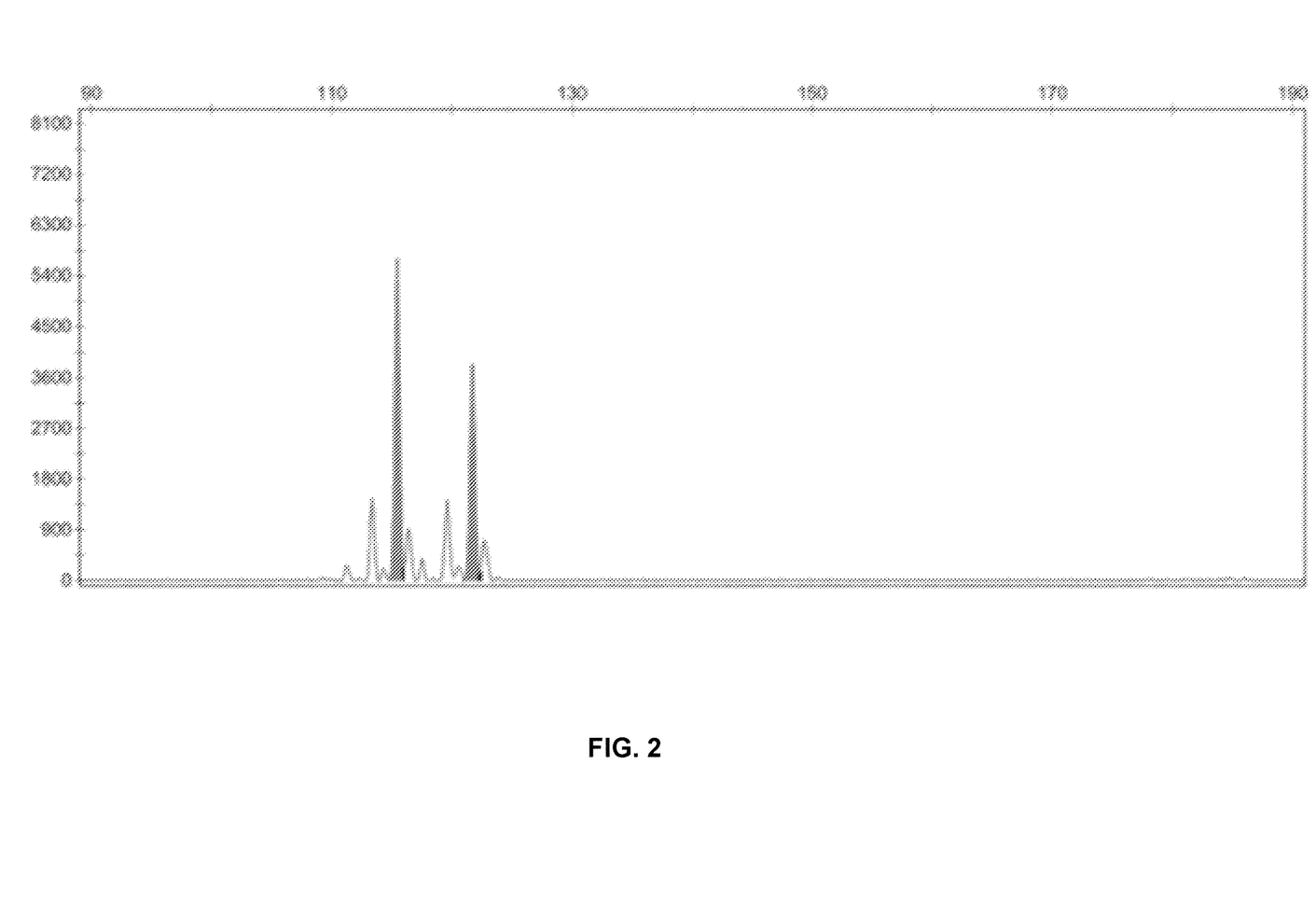
FIG. 2 shows the electrophoresis results of sample 8 at SW122 locus under fluorescent label 5'-HEX.
Figure 3:
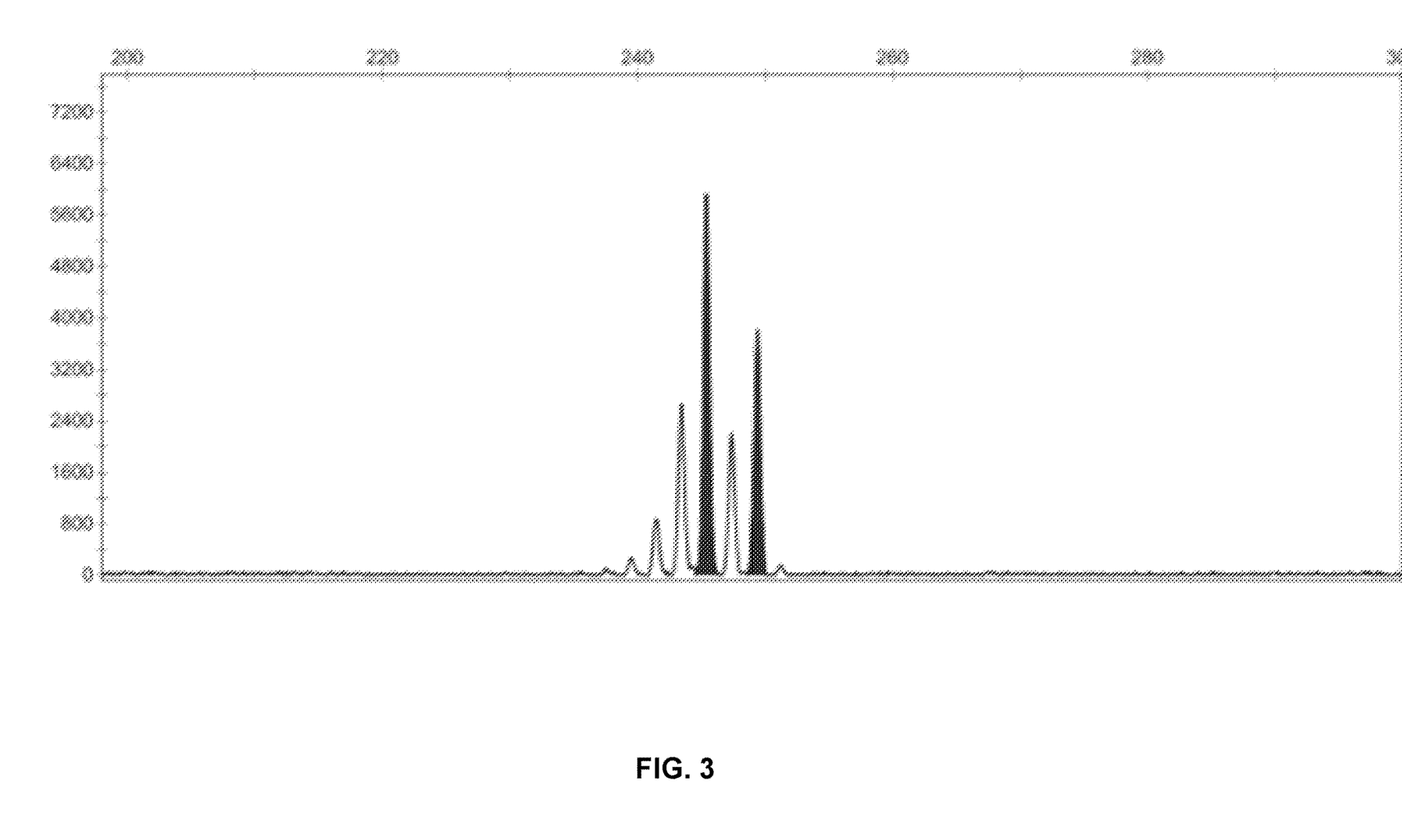
FIG. 3 shows the electrophoresis results of sample 95 at S0090 locus under fluorescent label 5'-TAMRA.

PCR reaction is performed with 25 μL reaction system, including 1 μL upstream primer, 1 μL downstream primer, 1 μL dNTR (mix), 2.5 μL Taq Buffer (with MgCl2), 0.5 μL Taq enzyme, 19 μL ddH2O. The PCR procedure is set as follows: 95° C. pre denaturation (3 min), 10 cycles (94° C. denaturation (30 sec), 60° C. annealing (30 sec), 72° C. extension (30 sec)), 35 cycles (94° C. denaturation (30 sec), 55° C. annealing (30 sec), 72° C. extension (30 sec)), 72° C. repair extension (8 min))

trophoresis results of sample 65 at S0155 locus, indicating that sample 65 is homozygous. There are two peaks (111/118 bp) in the electrophoresis results of sample 8 at SW122 locus, indicating that sample 8 is heterozygous. Sample 95 has two peaks at S0090, indicating that sample 95 is heterozygous.

The alleles and gene frequencies of microsatellite loci in Anqing six-end-white pig population are shown in Table 2 (they are named allele A to allele L respectively according to the order of fragment size from low to high).

TABLE 2

Statistics of alleles and gene frequencies of 14 microsatellite loci in Anqing six-end-white pig population

| Allele\Loci | S0155 | SW240 | SW72 | S0227 | SW963 | SW122 | S0101 | S0255 | S0386 | S0090 | S0355 | SW24 | S0026 | SW2156 |
|---|---|---|---|---|---|---|---|---|---|---|---|---|---|---|
| Allele A | 0.0969 | 0.0053 | 0.2448 | 0.2755 | 0.0263 | 0.3041 | 0.0465 | 0.1684 | 0.2296 | 0.1378 | 0.1833 | 0.0412 | 0.1701 | 0.0227 |
| Allele B | 0.0663 | 0.0947 | 0.4323 | 0.0051 | 0.0105 | 0.1340 | 0.0581 | 0.2143 | 0.1071 | 0.1582 | 0.0889 | 0.0258 | 0.0928 | 0.1193 |
| Allele C | 0.0408 | 0.0158 | 0.0625 | 0.0612 | 0.1105 | 0.0361 | 0.1047 | 0.0459 | 0.0612 | 0.3878 | 0.0222 | 0.0155 | 0.2113 | 0.2500 |
| Allele D | 0.1174 | 0.0842 | 0.2292 | 0.1582 | 0.1211 | 0.1340 | 0.0116 | 0.1786 | 0.1276 | 0.1735 | 0.0222 | 0.1753 | 0.0309 | 0.1648 |
| Allele E | 0.3724 | 0.0474 | 0.0312 | 0.3673 | 0.1895 | 0.2062 | 0.2209 | 0.0102 | 0.0255 | 0.0153 | 0.0889 | 0.0619 | 0.4794 | 0.0909 |
| Allele F | 0.1684 | 0.0684 |  | 0.1173 | 0.0526 | 0.0309 | 0.0233 | 0.0918 | 0.4235 | 0.1122 | 0.1889 | 0.4742 | 0.0155 | 0.1080 |
| Allele G | 0.1378 | 0.3000 |  | 0.0154 | 0.3684 | 0.0155 | 0.0174 | 0.0204 | 0.0255 | 0.0152 | 0.2611 | 0.0412 |  | 0.0170 |
| Allele H |  | 0.1105 |  |  | 0.0947 | 0.0155 | 0.0291 | 0.0153 |  |  | 0.1445 | 0.0103 |  | 0.0170 |
| Allele I |  | 0.0421 |  |  | 0.0264 | 0.1237 | 0.3837 | 0.1122 |  |  |  | 0.0567 |  | 0.0739 |
| Allele J |  | 0.1421 |  |  |  |  | 0.1047 | 0.1020 |  |  |  | 0.0979 |  | 0.0455 |
| Allele K |  | 0.0895 |  |  |  |  |  | 0.0357 |  |  |  |  |  | 0.0909 |
| Allele L |  |  |  |  |  |  |  | 0.0052 |  |  |  |  |  |  |

1.5 Capillary Electrophoresis Detection of PCR Products

ABI3730xl gene sequencer is used to perform capillary electrophoresis on PCR products, and Genemapper software is used to read and analyze the capillary electrophoresis results to judge the allele size and genotype of each sample at each microsatellite locus.

1.6 Data Processing and Analysis

The genotypes of microsatellite loci in Anqing six-end-white pigs are sorted out. Use POPgene3.2 software to analyze microsatellite loci genetic information based on the following information including: count of alleles, effective count of alleles, observed homozygote, expected homozygote, observed heterozygosity, expected heterozygosity, Shannon's information index, Hard Weinberg equilibrium test, and use PIC_Cale0.6 software to calculate the polymorphism information content. The present disclosure regards each sample as a group. Using the DiploidDate program to calculate the NEI genetic distance between the individual, and obtain the affinity cluster map constructed by the Unweight Pair-GROUP Method with Arithmetic Mean (UPGMA). Cervus 3.07 software is used to calculate the null allele frequency and combined exclusion probability of 14 microsatellite loci. The exclusion probability is calculated by an equation of 1−combined exclusion probability.

2 Results and Analysis

2.1 Genetic Diversity Analysis of 14 Microsatellite Loci in Anqing Six-End-White Pigs The present disclosure selects 14 microsatellite loci to analyze the genetic diversity of 98 Anqing six-end-white pigs. The capillary electrophoresis results of PCR products at some microsatellite loci are shown in FIGS. 1, 2 and 3. For example, there is only one peak (161 bp) in the elec- A total of 119 alleles are detected at 14 loci, and the average number of alleles at each locus is 8.5. Among them, the number of alleles at S0255 locus is the most (n=12), the corresponding fragment range is 167 bp-191 bp, and the number of alleles at SW72 locus is the least (n=5), and the corresponding fragment range is 99 bp-113 bp. Among the 14 loci, the allele B (100 bp) of SW72 locus has the highest allele frequency of 0.4323 in Anqing six-end-white pig population. The allele L (191 bp) of S0255 locus has the lowest allele frequency of 0.0052 in Anqing six-end-white pig population. The count of alleles with allele frequency greater than 0.1 is 2-5.

The genetic diversity analysis of 14 microsatellite loci in Anqing six-end-white pigs is shown in Table 3. The count of effective alleles at each locus is 3.1927-7.1078, and the average count of effective alleles is 4.8161, of which the count of effective alleles at S0026 is the least and the count of effective alleles at SW2156 is the most. The observed homozygosity of each locus is between 0.1684-0.6421, among which the observed homozygosity value of SW240 is the smallest and that of SW963 is the largest. The expected homozygosity of each locus is 0.3579-0.8316, among which the expected homozygosity value of SW963 is the smallest and that of SW240 is the largest. The observed heterozygosity of each locus ranges from 0.1358 to 0.3097. The observed heterozygosity of SW2156 is the smallest and that of S0026 is the largest. The expected heterozygosity of each locus ranges from 0.6903 to 0.8626, the expected heterozygosity of S0026 is the lowest, and the expected heterozygosity of S0255 is the highest.

TABLE 3

Genetic information analysis of 14 microsatellite loci in Anqing six-end-white pig population

| Loci | S0155 | SW240 | SW72 | S0227 | SW963 | SW122 | S0101 | S0255 | S0386 | S0090 | S0355 | SW24 | S0026 | SW2156 |
|---|---|---|---|---|---|---|---|---|---|---|---|---|---|---|
| Na | 7 | 11 | 5 | 7 | 9 | 9 | 10 | 12 | 7 | 7 | 8 | 10 | 6 | 11 |
| Ne | 4.6452 | 6.4326 | 3.2873 | 3.9425 | 4.7227 | 5.2919 | 4.4380 | 7.0540 | 3.7759 | 4.2104 | 5.7103 | 3.614 | 3.1927 | 7.1078 |
| Hom (Obs) | 0.2347 | 0.1684 | 0.3021 | 0.3571 | 0.6421 | 0.1856 | 0.2326 | 0.4592 | 0.6020 | 0.2857 | 0.4333 | 0.3299 | 0.3299 | 0.3864 |
| Hom (Exp) | 0.7653 | 0.8316 | 0.6979 | 0.6429 | 0.3579 | 0.8144 | 0.7674 | 0.5408 | 0.3980 | 0.7143 | 0.5667 | 0.6701 | 0.6701 | 0.6136 |
| Het (Obs) | 0.2113 | 0.1510 | 0.3006 | 0.2498 | 0.2076 | 0.1848 | 0.2208 | 0.1374 | 0.2611 | 0.2336 | 0.1705 | 0.2729 | 0.3097 | 0.1358 |
| Het (Exp) | 0.7887 | 0.8490 | 0.6994 | 0.7502 | 0.7924 | 0.8152 | 0.7792 | 0.8626 | 0.7389 | 0.7664 | 0.8295 | 0.7271 | 0.6903 | 0.8642 |
| PIC | 0.7591 | 0.8293 | 0.6445 | 0.7069 | 0.7636 | 0.7866 | 0.7482 | 0.8424 | 0.7003 | 0.7307 | 0.8018 | 0.6985 | 0.6444 | 0.8446 |
| I | 1.7291 | 2.0840 | 1.3263 | 1.5281 | 1.7997 | 1.8411 | 1.7944 | 2.1130 | 1.5619 | 1.6094 | 1.8554 | 1.6903 | 1.3748 | 2.1314 |
| H-W | ** |  |  | ** | ** | ** |  | ** | ** |  | ** |  |  | ** |

Note:

Na (count of observed alleles); Ne (count of effective alleles); Hom (Obs) observed homozygosity; Hom (Exp) expected homozygosity; Het (Obs) observed heterozygosity; Het (Exp) expected heterozygosity; I: Shannon index; PIC: polymorphic information content; H-W: Hard-Weinberg equilibrium testing,  indicates that the locus has not reached H-W dynamic equilibrium, and no  mark indicates that the locus has reached H-W dynamic equilibrium.

The Shannon index of each locus is between 1.3263-2.1314, the Shannon index of SW72 is the lowest, and the Shannon index of SW2156 is the highest. The polymorphic information content of each locus ranges from 0.6444 to 0.8424. The polymorphic information content of S0026 is the lowest and that of S0255 is the highest. Each locus is subject to chi-square test to study whether it is in hard Weinberg dynamic equilibrium. Through calculation, S0155, S0227, SW963, SW122, S0255, S0386, S0355 and SW2156 are not in Hard-Weinberg dynamic equilibrium. SW240, SW72, S0101, S0090, SW24, S0026 are in Hard-Weinberg dynamic equilibrium.

2.2 Pedigree Division and Paternity Testing Based on SSR Markers

According to Nei's genetic distance calculation results, the phylogenetic tree of 98 Anqing six-end-white pigs is constructed. It can be found that the samples in the examples may be divided into 7 groups, which is consistent with the pedigree composition records of the protected population in the breeding farm. Nei's genetic distance and genetic consistency coefficient among some samples are shown in Table 4. The results show that there is a negative correlation between genetic consistency coefficient and genetic distance coefficient.

TABLE 4

Nei's genetic distance and genetic consistency coefficient of samples 1-12

| Sample ID | 1 | 2 | 3 | 4 | 5 | 6 | 7 | 8 | 9 | 10 | 11 | 12 |
|---|---|---|---|---|---|---|---|---|---|---|---|---|
| 1 | *** | 0.2165 | 0.1369 | 0.6790 | 0.2646 | 0.1021 | 0.0990 | 0.2552 | 0.1485 | 0.2406 | 0.2552 | 0.2054 |
| 2 | 1.5301 | *** | 0.4743 | 0.0811 | 0.2778 | 0.4419 | 0.1143 | 0.3830 | 0.4287 | 0.2500 | 0.2946 | 0.4216 |
| 3 | 1.9883 | 0.7458 | *** | 0.1795 | 0.4480 | 0.4472 | 0.2712 | 0.3913 | 0.4339 | 0.3162 | 0.2236 | 0.3250 |
| 4 | 0.3871 | 2.5119 | 1.7173 | *** | 0.4056 | 0.1434 | 0.1113 | 0.1434 | 0.1113 | 0.3515 | 0.2007 | 0.1026 |
| 5 | 1.3295 | 1.2809 | 0.8030 | 0.9025 | *** | 0.3241 | 0.3144 | 0.2357 | 0.3716 | 0.5278 | 0.2946 | 0.3162 |
| 6 | 2.2822 | 0.8166 | 0.8047 | 1.9422 | 1.1267 | *** | 0.3638 | 0.5000 | 0.4548 | 0.4714 | 0.5000 | 0.3634 |
| 7 | 2.3125 | 2.1686 | 1.3050 | 2.1957 | 1.1570 | 1.0111 | *** | 0.1213 | 0.4412 | 0.2572 | 0.4244 | 0.4067 |
| 8 | 1.3659 | 0.9597 | 0.9383 | 1.9422 | 1.4452 | 0.6931 | 2.1098 | *** | 0.5760 | 0.2946 | 0.3125 | 0.2236 |
| 9 | 1.9070 | 0.8469 | 0.8350 | 2.1957 | 0.9900 | 0.7880 | 0.8183 | 0.5516 | *** | 0.3430 | 0.2122 | 0.4610 |
| 10 | 1.4248 | 1.3863 | 1.1513 | 1.0456 | 0.6391 | 0.7520 | 1.3577 | 1.2220 | 1.0700 | *** | 0.3241 | 0.2372 |
| 11 | 1.3659 | 1.2220 | 1.4979 | 1.6058 | 1.2220 | 0.6931 | 0.8570 | 1.1632 | 1.5501 | 1.1267 | *** | 0.1898 |
| 12 | 1.5828 | 0.8636 | 1.1239 | 2.2769 | 1.1513 | 1.0124 | 0.8996 | 1.4979 | 0.7744 | 1.4390 | 1.2747 | *** |

Note:

the genetic consistency coefficient is at the top of the table (i.e., above the labels of *), and the genetic distance coefficient is at the bottom of the table (i.e., below the labels of *).

The combined exclusion probability of 14 microsatellite loci is shown in Table 5. When the genotype of a candidate parent and its offspring is known (NE-1P), the exclusion probability of each locus is 0.276-0.419, and the cumulative exclusion probability of 14 loci is 0.9995. The genotype of another different candidate parent with different sex and its offspring is known (NE-2P), the exclusion probability of each locus is 0.448-0.713, and the cumulative exclusion probability of 14 loci is 0.9999. The genotype of both candidate parents and the corresponding offspring is known (NE-PP), the exclusion probability of each locus is 0.626-0.887, and the cumulative exclusion probability of 14 loci is 0.9999.

In the 14 microsatellite loci selected by the present disclosure, a total of 119 alleles are observed in Anqing six-end-white pig population, and the average count of alleles at each locus is 8.500±2.1031. The average count of effective alleles is 4.8162±1.3217. The average count of effective alleles of microsatellite loci in Anqing six-end-white pigs is higher than that of other types of local pigs in Anhui Province (e.g., Wei pig, Wannan black pig and Wannan flower pig), and also higher than that of some types of local pigs outside Anhui Province, such as Fengjing pig, Saba pig, Dahe pig and Bama Xiang pig. By detecting the Ne/Na ratio of each locus, it is found that the Ne/Na ratio of S0355 locus is the highest, i.e., 0.7138 and the ratio of SW24 locus is the lowest, i.e., 0.3614, indicating that the alleles of S0355 locus are evenly distributed in Anqing six-end-white pig population. In addition, the number of alleles of S0227 locus in Anqing six-end-white pig population is 7 while only 4 alleles are detected in pigs in Thailand. The alleless of other microsatellite loci in Anqing six-end-white pig are also different from those of Mexican hairless pig, Gubacrior pig and Iberian pig. This shows that there is specificity in the distribution of alleles of the 14 loci in Anqing six-end-white pig population.

The count of effective alleles, polymorphic information content and heterozygosity are important indicators to study population genetic variation. Hardy Weinberg dynamic equilibrium may reflect population migration and selection. Heterozygosity may be used to measure the degree of variation of the population. The lower the value of heterozygosity is, the less genetic variation and diversity of the population are. The average expected heterozygosity of 14 microsatellite loci in Anqing six-end-white pigs is 0.7824±0.0573, which is in the middle level among local pigs in China. Polymorphic information content may be used as one of the indicators to measure the polymorphism of loci. If the value of polymorphic information content is high, it means that the proportion of heterozygotes in the population is high, and its genetic potential is also greater. The polymorphic information content of 14 microsatellite loci in Anqing six-end-white pig population is higher than 0.5, and the average polymorphic information content is 0.74±0.06. When a genetic locus reaches H-W dynamic equilibrium, its allele frequency and genotype frequency may be inherited stably in the population. In the present disclosure, among the 14 microsatellite loci in Anqing six-end-white pig population, eight loci such as S0155 do not reach H-W dynamic equilibrium, and six loci such as SW240 reach H-W dynamic equilibrium. A total of 14 microsatellite loci are selected for polymorphism detection, and each locus belongs to different chromosomes, which has little possibility of linkage with each other. The genetic distance clustering map drawn according to the microsatellite results may distinguish 98 Anqing six-end-white pigs into 7 pedigrees, which is consistent with the introduction records at the beginning of introducing the conservation population, indicating that the reliability of methods and/or kits of the present disclosure is high. The cumulative exclusion probability of NE-1P, NE-2P, NE-PP of the 14 microsatellite loci selected by the present disclosure is more than 99%, meeting the requirements of paternity testing among different individuals in production practice.

It can be seen that the above embodiment is only an exemplary embodiment adopted to illustrate the principle of the present disclosure. However, the present disclosure is not limited to this. Those skilled in the art can make various improvements and changes without departing from the essence of the present disclosure, which also belong to the protection scope of the present disclosure.

TABLE 5

| Exclusion probability of 14 microsatellite loci | | | | | | |
|---|---|---|---|---|---|---|
| Loci | NE-1P | NE-2P | NE-PP | NE-I | NE-SI | F (Null) |
| S0155 | 0.419 | 0.6 | 0.79 | 0.929 | 0.625 | 0.0115 |
| SW240 | 0.534 | 0.7 | 0.874 | 0.96 | 0.662 | 0.0019 |
| SW72 | 0.278 | 0.448 | 0.626 | 0.858 | 0.564 | −0.0080 |
| S0227 | 0.344 | 0.522 | 0.708 | 0.896 | 0.597 | 0.0741 |
| SW963 | 0.431 | 0.61 | 0.8 | 0.932 | 0.629 | 0.3810 |
| SW122 | 0.456 | 0.632 | 0.814 | 0.94 | 0.64 | −0.0060 |
| S0101 | 0.408 | 0.588 | 0.782 | 0.923 | 0.618 | 0.0055 |
| S0255 | 0.552 | 0.713 | 0.879 | 0.963 | 0.669 | 0.2350 |
| S0386 | 0.343 | 0.524 | 0.719 | 0.896 | 0.592 | 0.2846 |
| S0090 | 0.379 | 0.56 | 0.75 | 0.913 | 0.611 | 0.0353 |
| S0355 | 0.482 | 0.655 | 0.831 | 0.947 | 0.65 | 0.1759 |
| SW24 | 0.351 | 0.537 | 0.744 | 0.901 | 0.589 | 0.0410 |
| S0026 | 0.276 | 0.453 | 0.643 | 0.859 | 0.557 | 0.0173 |
| SW2156 | 0.562 | 0.722 | 0.887 | 0.929 | 0.625 | 0.1713 |
| Cumulative exclusion probability | 0.9995 | 0.9999 | 0.9999 | 0.9999 | 0.9999 | |

Note:
NE-1 denotes an average non-exclusion probability for identity of two unrelated individuals; NE-SI denotes an average non-exclusion probability for identity of two siblings; F (Null) denotes an estimated null allele frequency.

What is claimed is:

1. A kit for pedigree division and paternity testing of Anqing six-end-white pigs, comprising:

primers configured to amplify 14 simple sequence repeats (SSR) loci which comprises: a S0155 microsatellite locus on chromosome 1, a SW240 microsatellite locus on chromosome 2, a SW72 microsatellite locus on chromosome 3, a S0227 microsatellite locus on chromosome 4, a SW963 microsatellite locus on chromosome 5, a SW122 microsatellite locus on chromosome 6, a S0101 microsatellite locus on chromosome 7, a S0225 microsatellite locus on chromosome 8, a S0386 microsatellite locus on chromosome 11, a S0090 microsatellite locus on chromosome 12, a S0355 microsatellite locus on chromosome 15, a S0026 microsatellite locus on chromosome 16, a SW24 microsatellite locus on chromosome 17, and a SW2156 microsatellite locus on sex chromosome, wherein the primers comprise: a forward primer sequence of the S0155 microsatellite locus shown in SEQ ID No. 1 and a reverse primer sequence of the S0155 microsatellite locus shown in SEQ ID No. 2; a forward primer sequence of the SW240 microsatellite locus shown in SEQ ID No. 3 and a reverse primer sequence of the SW240 microsatellite locus shown in SEQ ID No. 4; a forward primer sequence of the SW72 microsatellite locus shown in SEQ ID No. 5 and a reverse primer sequence of the SW72 microsatellite locus shown in SEQ ID No. 6; a forward primer sequence of the SW227 microsatellite locus shown in SEQ ID No. 7 and a reverse primer sequence of the SW227 microsatellite locus shown in SEQ ID No. 8; a forward primer sequence of the SW963 microsatellite locus shown in SEQ ID No. 9 and a reverse primer sequence of the SW963 microsatellite locus shown in SEQ ID No. 10; a forward primer sequence of the SW122 microsatellite locus shown in SEQ ID No. 11 and a reverse primer sequence of the SW122 microsatellite locus shown in SEQ ID No. 12; a forward primer sequence of the S0101 microsatellite locus shown in SEQ ID No. 13 and a reverse primer sequence of the S0101 microsatellite locus shown in SEQ ID No. 14; a forward primer sequence of the S0225 microsatellite locus shown in SEQ ID No. 15 and a reverse primer sequence of the S0225 microsatellite locus shown in SEQ ID No. 16; a forward primer sequence of the S0386 microsatellite locus shown in SEQ ID No. 17 and a reverse primer sequence of the S0386 microsatellite locus shown in SEQ ID No. 18; a forward primer sequence of the S0090 microsatellite locus shown in SEQ ID No. 19 and a reverse primer sequence of the S0090 microsatellite locus shown in SEQ ID No. 20; a forward primer sequence of the S0355 microsatellite locus shown in SEQ ID No. 21 and a reverse primer sequence of the S0355 microsatellite locus shown in SEQ ID No. 22; a forward primer sequence of the S0026 microsatellite locus shown in SEQ ID No. 23 and a reverse primer sequence of the S0026 microsatellite locus shown in SEQ ID No. 24; a forward primer sequence of the SW24 microsatellite locus shown in SEQ ID No. 25 and a reverse primer sequence of the SW24 microsatellite locus shown in SEQ ID No. 26; and a forward primer sequence of the SW2156 microsatellite locus shown in SEQ ID No. 27 and a reverse primer sequence of the SW2156 microsatellite locus shown in SEQ ID No. 28.

2. The kit of claim 1, wherein the primers configured to amplify the S0155 microsatellite locus, SW963 microsatellite locus, and S0386 microsatellite locus are fluorescent-labeled as 5'-FAM, the primers configured to amplify the SW240 microsatellite locus, the SW72 microsatellite locus, the SW122 microsatellite locus, the SW24 microsatellite locus, and the S0026 microsatellite locus are fluorescent-labeled as 5'-HEX, and the primers configured to amplify the S0227 microsatellite locus, the S0101 microsatellite locus, the S0090 microsatellite locus, and the S0355 microsatellite locus are fluorescent-labeled as 5'-TAMRA, a PCR annealing temperature of the primers configured to amplify the S0155 microsatellite locus, the SW240 microsatellite locus, the SW72 microsatellite locus, the S0227 microsatellite locus, the SW963 microsatellite locus, the S0101 microsatellite locus, the S0225 microsatellite locus, the S0386 microsatellite locus, the S0090 microsatellite locus, the S0355 microsatellite locus and the SW24 microsatellite locus is 55° C., the PCR annealing temperature of the primers configured to amplify the SW122 microsatellite locus is 58.5° C. and the annealing temperature of the primers configured to amply the SW2156 microsatellite locus is 60° C.

3. The kit of claim 2, comprising 1 μL upstream primer solution, 1 μL downstream primer solution, 1 μL mix dNTP solution, 2.5 μL MgCl$_2$ Taq Buffer, a 0.5 μL Taq enzyme solution, and 19 μL ddH$_2$O.

4. A method for pedigree division and paternity testing of Anqing six-end-white pigs, using the primers configured to amplify the 14 SSR loci in the kit of claim 3.

5. The method of claim 4, comprising:

collecting samples from the Anqing six-end-white pigs;

extracting DNA from the samples by using a rapid genomic DNA extraction kit;

performing PCR amplification with the primers to obtain PCR products;

detecting PCR products by capillary electrophoresis to obtain a detection result; and performing data processing and results analysis for the detection result.

6. The method of claim 5, wherein the performing data processing and results analysis for the detection result comprises:

using Popgene3.2 software to perform an analysis of a count of alleles, a count of effective alleles, an observed homozygosity, an expected homozygosity, an observed heterozygosity, an expected heterozygosity, a Shannon index and a hard Weinberg equilibrium index of each microsatellite locus;

using PIC_Cale0.6 software to calculate a polymorphic information content;

using a DiploidDate program to calculate a Nei's genetic distance between individuals; and obtaining a phylogenetic cluster diagram constructed by an unweighted pair-group method with arithmetic mean (UPGMA).

7. The method of claim 6, wherein the samples are collected from ears of the Anqing six-end-white pigs.

8. The method of claim 7, wherein the performing PCR amplification with the primers to obtain PCR products comprises:
- performing pre denaturation at 95° C. for 3 minutes;
- performing denaturation at 94° ° C. for 30 seconds, annealing at 60° ° C. for 30 seconds, performing extension at 72° ° C. for 30 seconds for 10 cycles;
- performing denaturation at 94° C. for 30 seconds, annealing at 55° ° C. for 30 seconds, performing extension at 72° ° C. for 30 seconds for 35 cycles; and
- performing repairing and extension at 72° ° C. for 8 minutes.

* * * * *